United States Patent
Kim et al.

(10) Patent No.: US 7,529,581 B2
(45) Date of Patent: May 5, 2009

(54) METHOD AND SYSTEM FOR CHARACTERIZING A REPRESENTATIVE CARDIAC BEAT USING MULTIPLE TEMPLATES

(75) Inventors: Jaeho Kim, Redmond, WA (US); Joseph Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 114 days.

(21) Appl. No.: 11/711,329

(22) Filed: Feb. 27, 2007

(65) Prior Publication Data

US 2007/0149889 A1    Jun. 28, 2007

Related U.S. Application Data

(62) Division of application No. 10/105,875, filed on Mar. 25, 2002, now Pat. No. 7,184,818.

(51) Int. Cl.
*A61B 5/04* (2006.01)

(52) U.S. Cl. .................................................. 600/515
(58) Field of Classification Search ................. 600/515
See application file for complete search history.

(56) References Cited

U.S. PATENT DOCUMENTS

| | | | |
|---|---|---|---|
| 4,336,810 A * | 6/1982 | Anderson et al. | 600/515 |
| 4,589,420 A * | 5/1986 | Adams et al. | 600/515 |
| 5,000,189 A | 3/1991 | Throne et al. | |
| 5,113,869 A | 5/1992 | Nappholz et al. | |
| 5,215,098 A * | 6/1993 | Steinhaus et al. | 600/515 |
| 5,215,099 A * | 6/1993 | Haberl et al. | 600/515 |
| 5,217,021 A | 6/1993 | Steinhaus et al. | |
| 5,447,519 A | 9/1995 | Peterson | |
| 5,779,645 A | 7/1998 | Olson et al. | |
| 5,817,027 A | 10/1998 | Arand et al. | |
| 5,857,977 A | 1/1999 | Caswell et al. | |
| 6,035,232 A | 3/2000 | Thong et al. | |
| 6,052,620 A | 4/2000 | Gillberg et al. | |
| 6,067,471 A | 5/2000 | Warren | |
| 6,076,014 A | 6/2000 | Alt | |
| 6,312,388 B1 | 11/2001 | Marcovecchio et al. | |
| 6,449,503 B1 * | 9/2002 | Hsu | 600/518 |
| 6,526,313 B2 | 2/2003 | Sweeney et al. | |
| 6,708,058 B2 | 3/2004 | Kim et al. | |
| 6,745,068 B2 | 6/2004 | Koyrakh et al. | |
| 7,062,315 B2 | 6/2006 | Koyrakh et al. | |

\* cited by examiner

*Primary Examiner*—Carl H. Layno
*Assistant Examiner*—Jon-Eric C. Morales
(74) *Attorney, Agent, or Firm*—Hollingsworth & Funk, LLC

(57) ABSTRACT

Providing a method and system for characterizing one beat of a patient's supraventricular rhythm. A plurality of templates is provided and updated using a plurality of qualified beats. Updating occurs by temporally aligning the shock channel waveforms of the template beats using rate channel fiducial points. The template beats are combined by point-by-point addition of the shock channel waveforms. The resultant updated template characterizes one of the patient's supraventricular conducted cardiac beats.

20 Claims, 12 Drawing Sheets

Slope is flat

METHOD AND SYSTEM FOR CHARACTERIZING A REPRESENTATIVE CARDIAC BEAT USING MULTIPLE TEMPLATES

RELATED PATENT DOCUMENT

This application is a division of U.S. patent application Ser. No. 10/105,875 filed on Mar. 25, 2002, to issue on Feb. 27, 2007 as U.S. Pat. No. 7,184,818 which is incorporated herein by reference.

FIELD OF THE INVENTION

The present invention relates generally to implantable medical devices and, more particularly, to generating, with an implantable medical device, a template characterizing a representative cardiac beat based upon a minimal number of beats.

BACKGROUND OF THE INVENTION

Rhythmic contractions of a healthy heart are normally controlled by the sinoatrial (SA) node, specialized cells located in the upper right atrium. The SA node is the normal pacemaker of the heart, typically initiating 60-100 heart beats per minute. When the SA node is pacing the heart normally, the heart is said to be in normal sinus rhythm (NSR).

A heart rhythm which deviates from normal sinus rhythm is an arrhythmia. Arrhythmia is a general term used to describe heart rhythm disturbances arising from a variety of physical conditions and disease processes. Bradycardia occurs when the heart rhythm is too slow and has a number of etiological sources including tissue damage due to myocardial infarction, exposure to toxins, electrolyte disorders, infection, drug effects, hypoglycemia or hypothyroidism. Bradycardia also may be caused by the sick sinus syndrome, wherein the SA node loses its ability to generate or transmit an action potential to the atria.

Tachycardia occurs when the rhythm is too fast. The origin of an aberrant tachyarrhythmic impulse may lie in either the atria or the ventricles. Supraventricular tachycardia is an atrial arrhythmia and is often caused by an extra conducting pathway between the atria and ventricles. Such a pathway can allow retrograde conduction or electrical impulses from the ventricles into the atria. The extra pathway in combination with the normal pathway forms a conducting loop that modifies the normal heart rhythm. Atrial flutter is caused due to electrical impulses circulating in the atria. Atrial fibrillation occurs when the pulses occur in the atria at irregular intervals and usually at a rate of greater than 300 impulses per minute. As a result, pulses reaching the AV node and thus the ventricles are also irregular, causing irregular contractions of the ventricles at an increased rate.

Ventricular tachycardia occurs when a pulse is initiated in the ventricular myocardium with a rhythm more rapid than the normal rhythm of the SA node. Ventricular tachycardia (VT), for example, is characterized by a rapid heart beat, 150 to 250 beats per minute and typically results from damage to the ventricular myocardium from a myocardial infarction. Ventricular tachycardia can quickly degenerate into ventricular fibrillation (VF). Ventricular fibrillation is a condition denoted by extremely rapid, nonsynchronous contractions of the ventricles. The rapid and erratic contractions of the ventricles cannot effectively pump blood to the body and the condition is fatal unless the heart is returned to sinus rhythm within a few minutes.

Implantable cardioverter/defibrillators (ICDs) have been used as an effective treatment for patients with serious arrhythmias. ICDs are able to recognize and treat arrhythmias with a variety of tiered therapies. These tiered therapies include providing anti-tachycardia pacing or cardioversion energy for treating ventricular tachycardia and defibrillation energy for treating ventricular fibrillation. To effectively deliver these treatments, the ICD must first identify the type of arrhythmia that is occurring, after which appropriate therapy is provided to the heart. To apply the proper therapy in responding to an episode of arrhythmia, the ICD may compare sensed cardiac signals to a previously stored cardiac waveform. The stored cardiac waveform must accurately characterize a patient's true supraventricular rhythm (SVR) to properly identify potentially fatal deviations.

Various methods have been used to characterize a patient's supraventricular rhythm. Previously described methods often require the acquisition of a relatively large number of heart beat samples to accurately characterize the patient's SVR. These techniques are not suitable for use in all cases. When the heart is being paced, for example, the paced beats are typically discarded from use in template formation. A large number of supraventricular beats may be difficult to acquire for patients requiring intermittent or constant pacing pulses to be applied to the heart. Consequently, for these patients, a characterization of SVR cannot readily be generated or updated by previous methods.

For the reasons stated above, and for other reasons stated below which will become apparent to those skilled in the art upon reading the present specification, there is a need in the art for a method and device that reliably and accurately characterizes a patient's SVR requiring a minimal number of supraventricular beat samples. There exists a further need for such an approach that is adaptive and accommodates changes in the patient's SVR over time. The present invention fulfills these and other needs.

SUMMARY OF THE INVENTION

The present invention is directed to a method and device for generating a snapshot representative of one beat of a patient's supraventricular rhythm using a minimal number of beats. In accordance with one embodiment of the present invention, a number of templates are provided. The templates are selectively updated with qualified beats and are used to characterize the patient's supraventricular rhythm.

In another embodiment of the invention, a patient's supraventricular rhythm is characterized using a first template and a second template. A first template and a second template are provided. The first template is updated with qualified beats correlated to the first template and a first number of correlated beats associated with the first template is counted. The second template is updated with qualified beats correlated to the second template and a second number of correlated beats associated with the second template is counted. The first updated template is stored as a current template if the first number of correlated beats reaches a predetermined count prior to the second number of correlated beats reaching the predetermined count. The second updated template is stored as a current template if the second number of correlated beats reaches a predetermined count prior to the first number of correlated beats reaching the predetermined count. The current template represents one beat of the patient's supraventricular conducted beats.

Another embodiment of the invention is directed to a body implantable system for implementing SVR characterization. A lead system extends into a patient's heart and includes one or more electrodes. A detector system, coupled to the lead system, detects rate channel signals and shock channel signals sensed by the one or more electrodes. A control system is coupled to the detector system. The control system provides a number of templates, selectively updates the templates using a number of qualified beats, and characterizes the patient's supraventricular rhythm using the number of templates.

Another embodiment of the invention is directed to a body implantable system implementing an SVR characterization method using two templates. The body implantable system includes a lead system that extends into the heart. A detector system, coupled to the lead system, detects rate channel signals and shock channel signals. A control system, coupled to the lead system, provides a first and a second template. The control system updates the first template using qualified beats correlated to the first template and updates the second template using qualified beats correlated to the second template. A first number of correlated beats associated with the first template is counted and a second number of correlated beats associated with the second template is counted. The control system stores the first updated template as a current template if the first number of correlated beats associated with the first template reaches a predetermined count prior to the second number of correlated beats associated with the second template reaching the predetermined count. The control system stores the second updated template as a current template if the second number of correlated beats associated with the second template reaches a predetermined count prior to the first number of correlated beats associated with the first template reaching the predetermined count. The current template represents one beat of the patient's supraventricular conducted beats.

In another embodiment of the invention, a system for characterizing a patient's supraventricular rhythm includes means for providing a plurality of templates, means for selectively updating the plurality of templates using a plurality of qualified beats and means for characterizing the patient's supraventricular rhythm using a particular template of the plurality of updated templates.

Another embodiment of the invention is a system for characterizing a patient's supraventricular rhythm including means for providing a first template and a second template, means for detecting qualified beats, means for updating the first template or the second template using qualified beats correlated to the first template or the second template, means for counting a first number of correlated beats associated with the first updated template, means for counting a second number of correlated beats associated with the second template, means for storing the first updated template as a current template if the first number of correlated beats reaches a predetermined count prior to the second number of correlated beats reaching the predetermined count, and means for storing the second updated template as a current template if the second number of correlated beats reaches a predetermined count prior to the first number of correlated beats reaching the predetermined count. The current template represents one of the patient's supraventricular conducted beats.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
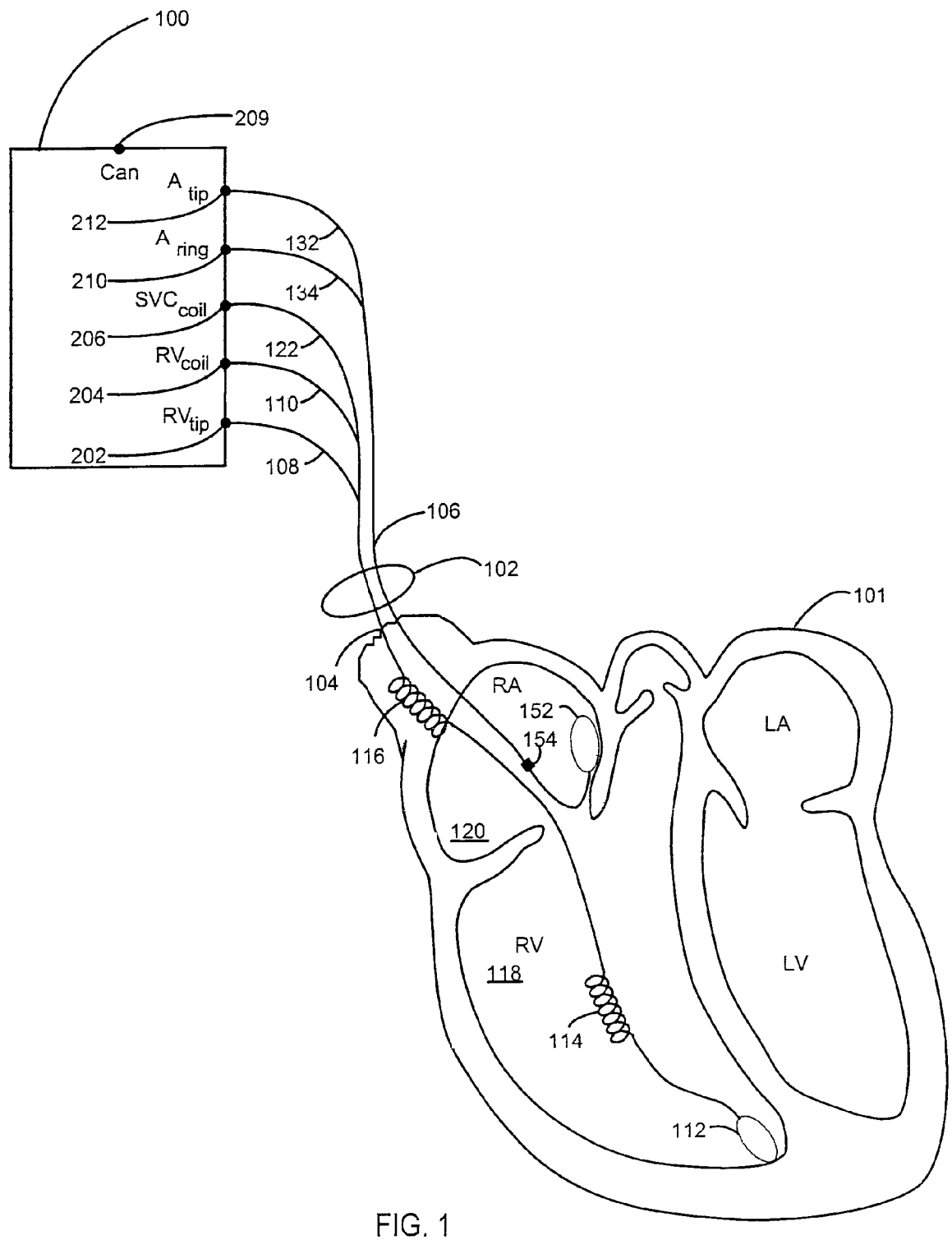
FIG. 1 is a partial view of one embodiment of an implantable medical device with an endocardial lead system extending into atrial and ventricular chambers of a heart.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

The embodiments of the present system illustrated herein are generally described as being implemented in an implantable cardiac defibrillator (ICD), which may operate in numerous pacing modes known in the art. The systems and methods of the present invention may also be implemented in other implantable medical devices that sense cardiac activity, such as pacemakers and cardiac monitors, for example.

In one embodiment, an implantable cardiac defibrillator that incorporates the systems and methods of the present invention is a dual chamber defibrillator. Various types of single and multiple chamber implantable cardiac defibrillators are known in the art and may implement an SVR characterization methodology of the present invention.

The systems and methods of the present invention may also be implemented in external cardioverter/monitor systems. Also, the present medical system can also be implemented in an implantable atrial cardioverter/defibrillator, which may include numerous pacing modes known in the art. Furthermore, although the present system is described in conjunction with an implantable cardiac defibrillator having a microprocessor-based architecture, it will be understood that the implantable cardiac defibrillator (or other device) may be implemented in any logic-based architecture, if desired.

Various methods have been used to characterize a patient's supraventricular rhythm. One such method is described in commonly owned U.S. patent application Ser. No. 09/845,987, filed Apr. 30, 2001, and entitled "Normal Cardiac Rhythm Template Generation System And Method," now U.S. Pat. No. 6,708,058 which is hereby incorporated herein by reference.

The present invention provides a system and method for monitoring a patient's electrocardiogram and producing a characterization of the patient's normal supraventricular conducted rhythm using fewer beats than previous methods. Producing such a characterization may be effected at any time for a number of different purposes. By way of example, the diagnosis of a patient's cardiac rhythms may be enhanced by comparing QRS complexes of a current cardiac rhythm to a characterization of the patient's supraventricular cardiac rhythm produced by employment of the methodologies of the present invention. By way of further example, the titration of drug dosage based on electrocardiographic properties of such a snapshot produced in accordance with the present invention may also be enhanced.

The methods of producing an accurate characterization of a patient's supraventricular rhythm may be used in combination with an automatic VT/SVT (ventricular tachyarrhythmia/supraventricular tachyarrhythmia) rhythm discrimination technique employed in an implantable cardioverter/defibrillator (ICD). Also, the methodologies of the present invention may be used as a component of an automatic Holter analysis system employed in an implantable pacemaker, for example. These and other applications may be enhanced by employment of the systems and methods of the present invention.

Referring now to FIG. 1 of the drawings, there is shown one embodiment of a medical device system which includes an implantable cardiac defibrillator 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under certain predetermined conditions to treat cardiac arrhythmias, including, for example, ventricular fibrillation of the heart 101. In an embodiment in which only monitoring of cardiac activity is performed, the intracardiac lead system 102 need not provide for the production of electrical energy to stimulate the heart 101.

The intracardiac lead system 102 includes one or more pacing electrodes and one or more intracardiac defibrillation electrodes. In the particular embodiment shown in FIG. 1, the intracardiac lead system 102 includes a ventricular lead system 104 and an atrial lead system 106. The ventricular lead system 104 includes an SVC-coil 116, an RV-coil 114, and an RV-tip electrode 112. The RV-coil 114, which is also referred to as an RV-ring electrode, is spaced apart from the RV-tip electrode 112, which is a pacing electrode. In one embodiment, the ventricular lead system 104 is configured as an integrated bipolar pace/shock lead.

The atrial lead system 106 includes an A-tip electrode 152 and an A-ring electrode 154. In one embodiment, the atrial lead system 106 is configured as an atrial J lead.

In this configuration, the intracardiac lead system 102 is positioned within the heart 101, with a portion of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

Additional pacing and defibrillation electrodes may also be included in the intracardiac lead system 102 to allow for various sensing, pacing, and defibrillation capabilities. For example, the intracardiac lead system 102 may include endocardial pacing and cardioversion/defibrillation leads (not shown) that are advanced into the coronary sinus and coronary veins to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Other intracardiac lead and electrode arrangements and configurations known in the art are also possible and considered to be within the scope of the present system.

The ventricular and atrial lead systems 104, 106 include conductors for communicating sense, pacing, and defibrillation signals between the cardiac defibrillator 100 and the electrodes and coils of the lead systems 104, 106. As is shown in FIG. 1, the ventricular lead system 104 includes a conductor 108 for transmitting sense and pacing signals between the RV-tip electrode 112 and an RV-tip terminal 202 within the cardiac defibrillator 100. A conductor 110 of the ventricular lead system 104 transmits sense signals between the RV-coil or ring electrode 114 and an RV-coil terminal 204 within the cardiac defibrillator 100. The ventricular lead system 104 also includes conductor 122 for transmitting sense and defibrillation signals between terminal 206 of the cardiac defibrillator 100 and the SVC-coil 116. The atrial lead system 106 includes conductors 132, 134 for transmitting sense and pacing signals between terminals 212, 210 of the cardiac defibrillator 100 and A-tip and A-ring electrodes 152 and 154, respectively.

Figure 2:
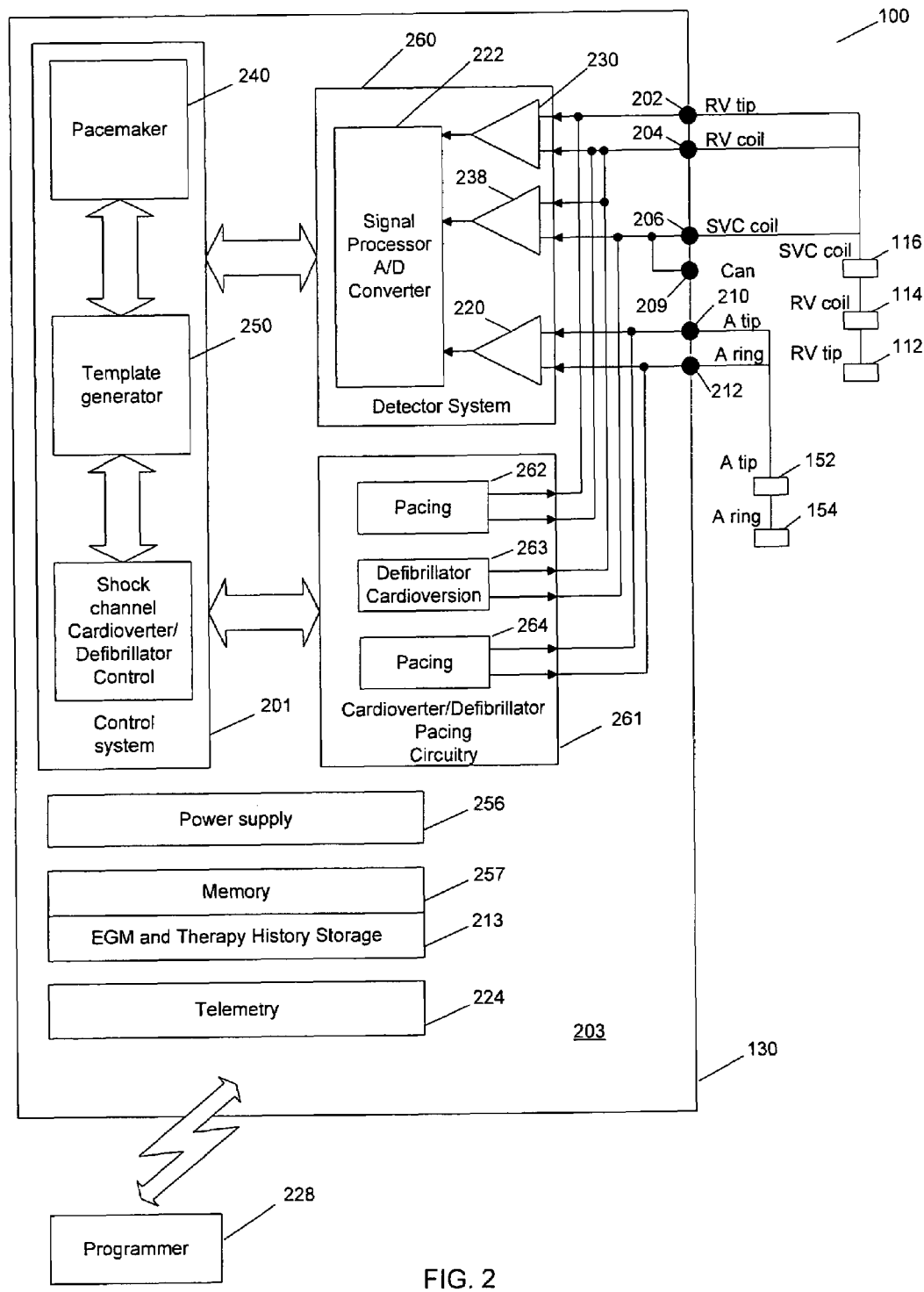
FIG. 2 is a block diagram of a cardiac defibrillator with which SVR characterization of the present invention may be implemented.

Referring now to FIG. 2, there is shown an embodiment of a cardiac defibrillator 100 suitable for implementing a supraventricular rhythm template generation methodology of the present invention. FIG. 2 shows a cardiac defibrillator divided into functional blocks. It is understood by those skilled in the art that there exist many possible configurations in which these functional blocks can be arranged. The example depicted in FIG. 2 is one possible functional arrangement. The cardiac defibrillator 100 includes cardiac defibrillator circuitry 203 for receiving cardiac signals from a heart 101 (not shown in FIG. 2) and delivering electrical energy to the heart. The cardiac defibrillator 100 includes terminals 202, 204, 206, 209, 210, and 212 for connecting to the electrodes and coils of the intracardiac lead system as previously discussed.

In one embodiment, the cardiac defibrillator circuitry 203 of the cardiac defibrillator 100 is encased and hermetically sealed in a housing 130 suitable for implanting in a human body as is known in the art. Power to the cardiac defibrillator 100 is supplied by an electrochemical battery 256 that is housed within the cardiac defibrillator 100. A connector block (not shown) is additionally attached to the housing 130 of the cardiac defibrillator 100 to allow for the physical and electrical attachment of the intracardiac lead system conductors to the cardiac defibrillator 100 and the encased cardiac defibrillator circuitry 203.

In one embodiment, the cardiac defibrillator circuitry 203 of the cardiac defibrillator 100 is a programmable microprocessor-based system, with a control system 201 and a memory circuit 257. The memory circuit 257 stores parameters for various pacing, defibrillation, and sensing modes and stores data indicative of cardiac signals received by other components of the cardiac defibrillator circuitry 203. The control system 201 and memory circuit 257 cooperate with other components of the cardiac defibrillator circuitry 203 to perform operations involving the generation of a template representing a snapshot of one beat of a patient's supraventricular rhythm according to the principles of the present invention, in addition to other sensing, pacing and defibrillation functions. A memory 213 is also provided for storing historical EGM and therapy data, which may be used on-board for various purposes and transmitted to an external programmer unit 228 as needed or desired.

Telemetry circuitry 224 is additionally coupled to the cardiac defibrillator circuitry 203 to allow the cardiac defibrillator 100 to communicate with an external programmer unit 228. In one embodiment, the telemetry circuitry 224 and the programmer unit 228 use a wire loop antenna and a radio frequency telemetric link, as is known in the art, to receive and transmit signals and data between the programmer unit 228 and cardiac defibrillator circuitry 203. In this manner, programming commands and instructions are transferred to the control system 201 of the cardiac defibrillator 100 from the programmer unit 228 during and after implant, and stored cardiac data pertaining to sensed arrhythmic episodes within the heart 101, template information, and subsequent therapy or therapies applied to correct the sensed arrhythmic event are transferred to the programmer unit 228 from the cardiac defibrillator 100, for example.

Cardiac signals sensed through use of the RV-tip electrode 112 are near-field signals or rate channel signals as are known in the art. More particularly, a rate channel signal is detected as a voltage developed between the RV-tip electrode 112 and the RV-coil 114. Rate channel signals developed between the RV-tip electrode 112 and the RV-coil 114 are referred to herein as rate channel signals or signals measured from the rate channel.

Cardiac signals sensed through use of one or both of the defibrillation coils or electrodes 114, 116 are far-field signals, also referred to as morphology or shock channel signals, as are known in the art. More particularly, a shock channel signal is detected as a voltage developed between the RV-coil 114 and the SVC-coil 116 or the can electrode 209. A shock channel signal may also be detected as a voltage developed between the RV-coil 114 and the SVC-coil 116 coupled to the can electrode 209. Shock channel signals developed using appropriate combinations of the RV-coil, SVC-coil, and can electrodes 114, 116 and 209 are sensed and amplified by a shock EGM amplifier 238 located in the detector system 260. The output of the EGM amplifier 238 is coupled to the control system 201 via the signal processor and A/D converter 222.

In the embodiment of the cardiac defibrillator 100 depicted in FIG. 2, RV-tip and RV-coil electrodes 112, 114 are shown coupled to a V sense amplifier 230 located within the detector system 260. Rate channel signals received by the V-sense amplifier 230 are communicated to the signal processor and A/D converter 222. The detector system serves to sense and amplify the rate channel signals. The signal processor and A/D converter 222 converts the R-wave signals from analog to digital form and communicates the signals to the control system 201.

A-tip and A-ring electrodes 152, 154 are shown coupled to an A-sense amplifier 220 located within the detector system 260. Atrial sense signals received by the A-sense amplifier 220 in the detector system 260 are communicated to an A/D converter 222. The A-sense amplifier serves to sense and amplify the A-wave signals. The A/D converter 222 converts the sensed signals from analog to digital form and communicates the signals to the control system 201.

The pacemaker 240 communicates pacing signals to the RV-tip and A-tip electrodes 112 and 152 according to a pre-established pacing regimen under appropriate conditions. Blanking circuitry (not shown) is employed in a known manner when a ventricular or atrial pacing pulse is delivered, such that the ventricular channel, atrial channel, and shock channel are properly blanked at the appropriate time and for the appropriate duration.

The cardiac defibrillator 100 depicted in FIG. 1 is well-suited for implementing a SVR characterization methodology according to the principles of the present invention. In the embodiment shown in FIG. 2, the SVR characterization processes of the present invention are carried out by the template generator 250. The shock channel and rate channel signals used for SVR characterization and related template operations are provided by the shock EGM amplifier 238 and the V-sense amplifier 230, respectively. It is understood that the required shock and rate channel signals may be developed and processed by components other than those depicted in FIG. 2 for system architectures that differ from the system architectures described herein.

Figure 3:
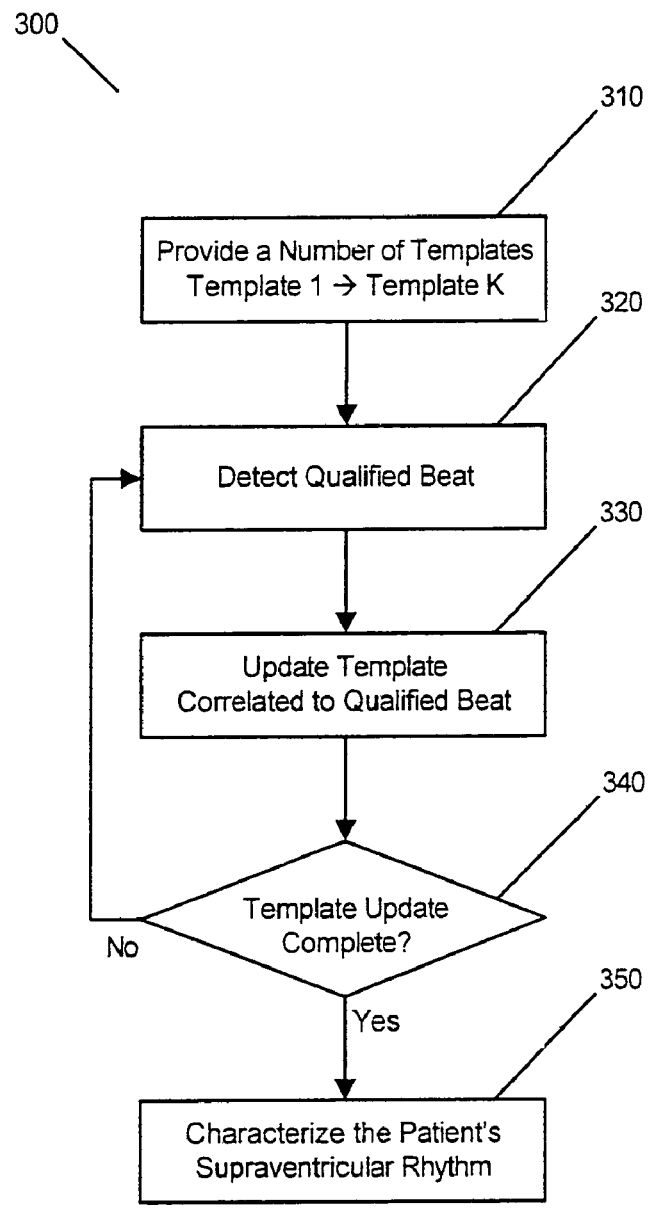
FIG. 3 is a flowchart of a method of characterizing supraventricular rhythm in accordance with an embodiment of the present invention.

FIG. 3 is a flowchart illustrating various processes for characterizing a patient's supraventricular rhythm according to an embodiment of the present invention. Characterization of a patient's supraventricular rhythm is accomplished through multiple stages, including, for example, iterative steps. The SVR characterization may be performed or updated periodically as needed or desired. According to the embodiment illustrated in the flowchart of FIG. 3, and in broad and general terms, upon commencement of SVR characterization, a number of templates is provided 310. A qualified beat is detected 320 and used to update 330 a template correlated to the beat. The process continues the loop 320 to 340 until the template update is complete. If the template update process is complete 340, the templates are used to characterize 350 the patient's supraventricular rhythm. The process depicted in FIG. 3 may be terminated for various reasons as described hereinbelow.

Figure 4:
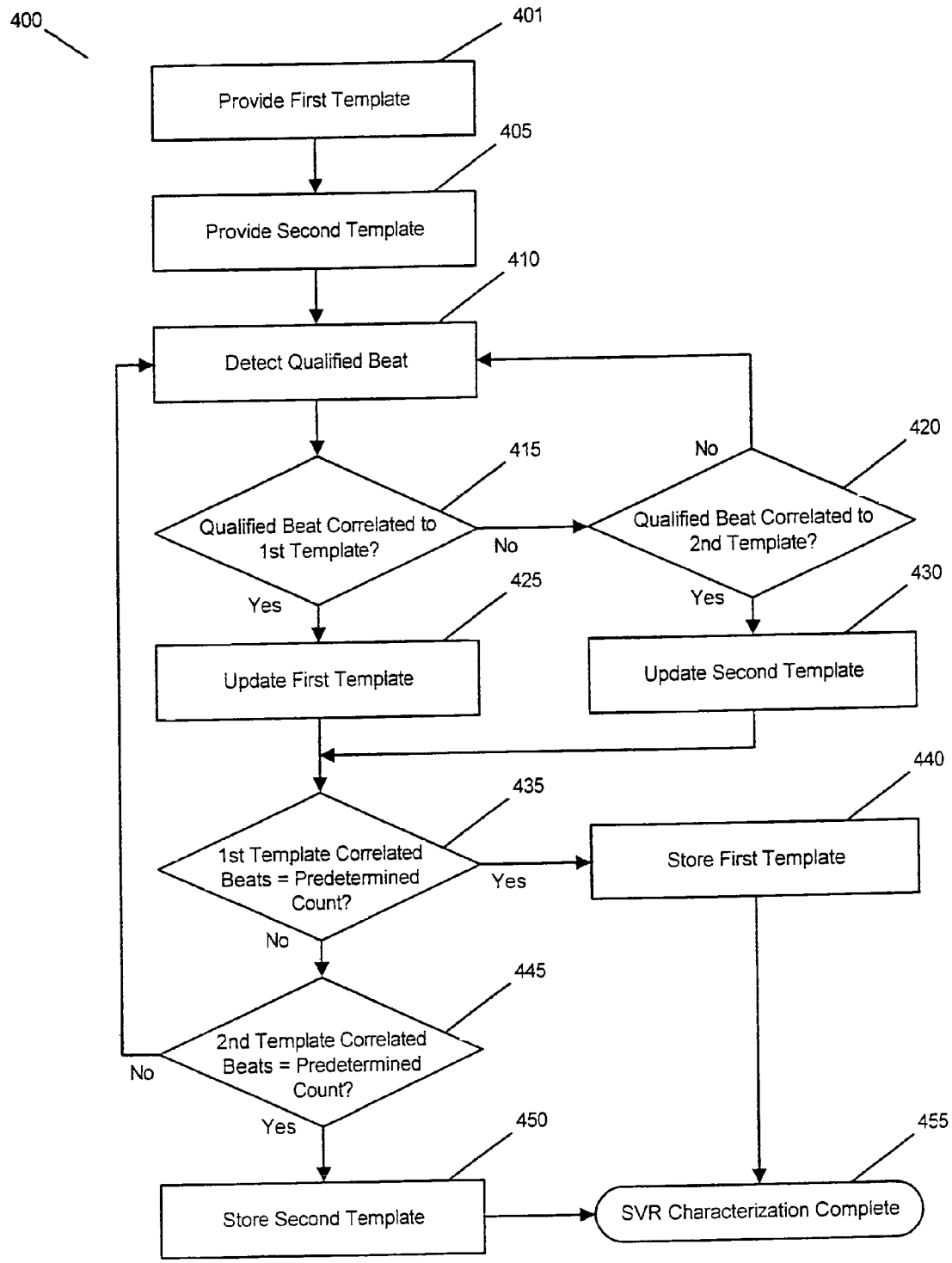
FIG. 4 is a flowchart of a method of characterizing supraventricular rhythm using two templates in accordance with an embodiment of the present invention.

Turning now to FIG. 4, various processes are illustrated for characterization of one beat of a patient's supraventricular rhythm according to another embodiment of the present invention. In this exemplary embodiment, two templates are used to characterize the supraventricular rhythm of a patient. Upon initiation of SVR characterization, a first template is provided 401 and a second template is provided 405. A qualified beat is detected 410. If the qualified beat is correlated to the first template 415, the first template is updated 425. If the qualified beat is uncorrelated to the first template, but is correlated to the second template 420, the second template is updated 430. If the beat is not correlated to either template, neither template is updated. The first and second templates continue to be updated 425, 430 by qualified beats in this manner until one of the templates is updated with a sufficient number of qualified beats.

If the number of beats correlated to the first template is equal to a predetermined count 435, the first template is saved 440 as a representation of the patient's supraventricular rhythm and SVR characterization is complete 455. If the number of beats correlated to the first template is less than a predetermined count 435 and the number of beats correlated to the second template is equal to a predetermined count 445, the second template is saved 450 as a representation of the patient's supraventricular rhythm and SVR characterization is complete 455.

Figure 5:
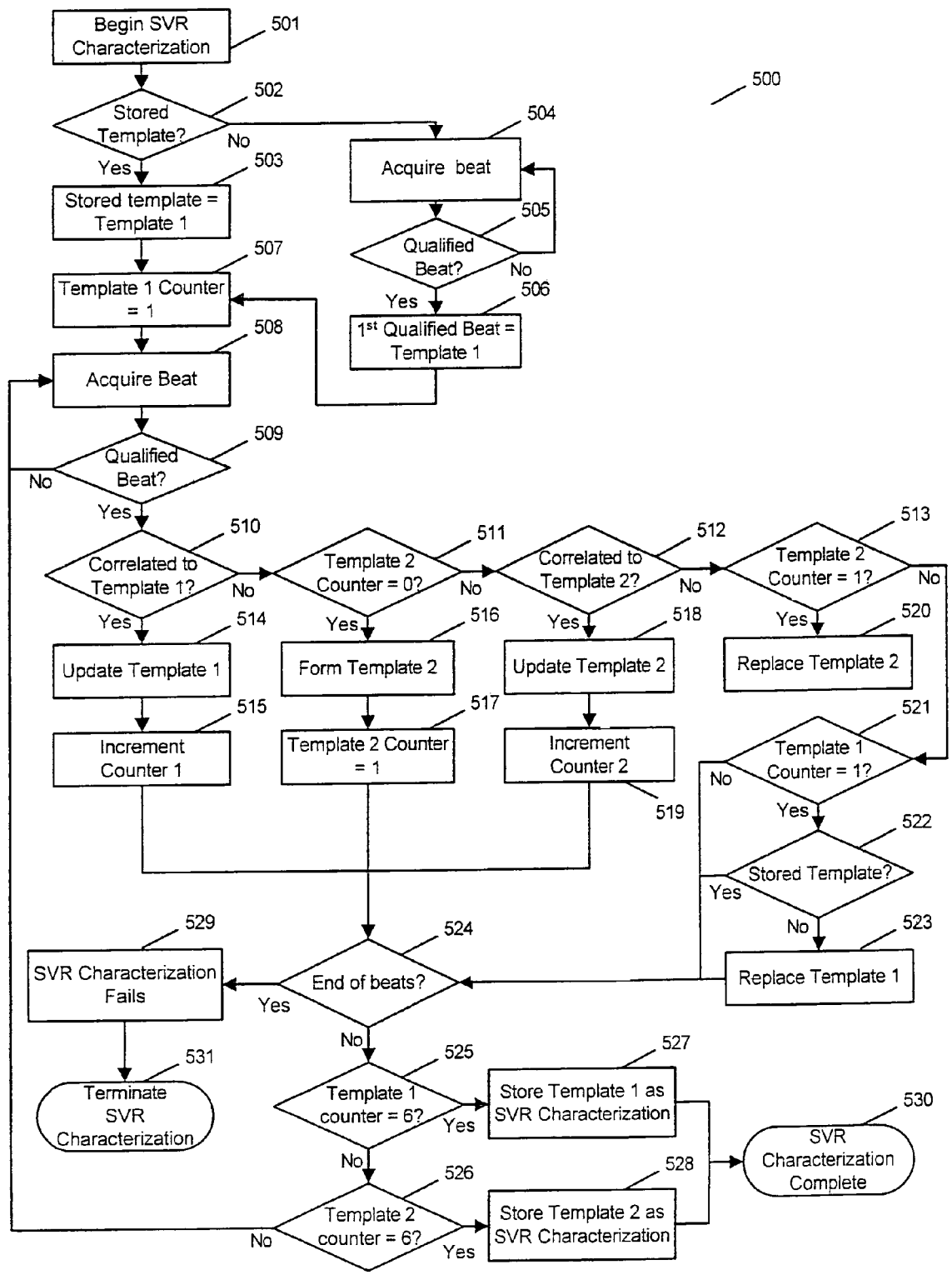
FIG. 5 is a more detailed flowchart of a method of characterizing supraventricular rhythm using two templates in accordance with an embodiment of the present invention.

FIG. 5 is a more detailed illustration of various steps associated with SVR characterization using two templates in accordance with an embodiment of the present invention. According to this embodiment, following commencement of SVR characterization 501, if a stored template exists 502, the stored template may be used as a first template 503 and a first template counter is set equal to one 507. Alternatively, a qualified beat is acquired 504, 505 and is used as the first template 506, and the first template counter is set equal to one 507.

According to the method of the exemplary embodiment, beats are acquired 508 until a qualified beat is detected 509. If the qualified beat correlates to the first template 510, the first template is updated 514 and the first template counter is incremented by one 515. If the qualified beat does not correlate to the first template 510, and the second template counter is zero 511, the qualified beat is used to form the second template 516 and the second template counter is set equal to one 517. If the second template has already been formed, and the qualified beat is correlated to the second template 512, the qualified beat is used to update the second template 518 and the second template counter is incremented by one 519.

If a qualified beat is not correlated to either template 510, 512, a template with a counter of one 513, 521 may be replaced 520, 523 by the qualified beat. If the second template counter has a value of one 513, then the second template is replaced 520 by the qualified beat. If the second template counter has a value greater than one 513 and the first template counter equals one 521, and the first template was not provided by retrieving a stored template from memory 522, then the first template may be replaced by the qualified beat 523. If the first template was provided by retrieving a stored template from memory 522, the control system may determine that the first template should be given a higher weight. In this situation, the first template may not be replaced by the qualified beat.

The loop beginning at block 508 is repeated until a predetermined number of beats is detected 524 or until one of the template counters is incremented to a value equal to a predetermined count, in this example, six counts 525, 526. If the template 1 counter is incremented to a value equal to six counts, 525, template 1 is stored as the characterization of the patient's supraventricular rhythm 527 and SVR characterization is complete 530. If the template 1 counter is not equal to six counts and the template 2 counter is equal to six counts 526, template 2 is stored as the characterization of the patient's supraventricular rhythm 528 and SVR characterization is complete 530. If neither template counter is incremented to a value equal to six counts before the predetermined number of beats is detected 524, the SVR characterization fails 529 and the characterization process is terminated 531.

Figure 6:
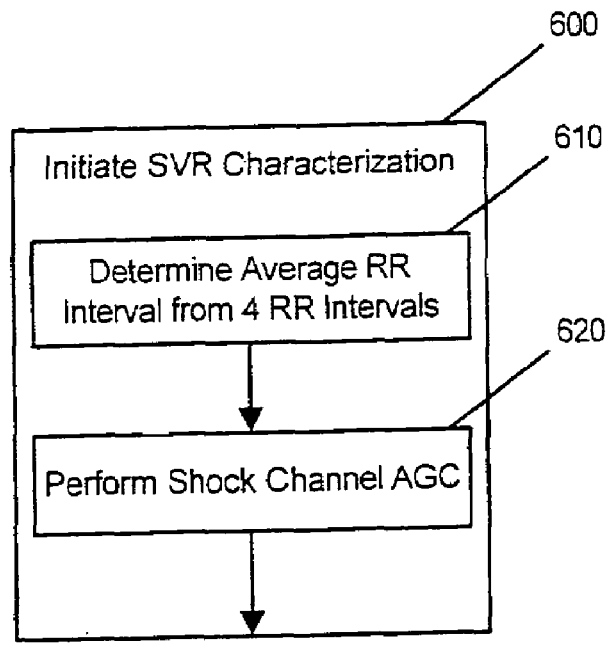
FIG. 6 is a flowchart of a method of initiating SVR characterization in accordance with an embodiment of the present invention.

FIG. 6 is a more detailed illustration of various processes 600 associated with initiating SVR characterization in accordance with an embodiment of the present invention. RR intervals are developed from the sensed rate channel signals. An RR interval is measured as an interval between Vs to Vs, Vs to Vp, Vp to Vs, or Vp to Vp events, where Vs is the ventricular sensed event detection time and Vp is the ventricular pace pulse delivery time.

The initial RR average (RRavg) may be calculated as the average of the first four RR intervals 610. In one embodiment, the RRavg is calculated as a running average as is characterized in Equation 1 below:

$$RRavg(I)=0.875*RRavg(I-1)+0.125*RR(I) \quad [1]$$

Equation 1 above represents one method for determining the RR average. Other methods are known in the art that can be used successfully to obtain the RR average.

A beat is classified as a "regular" beat when an RR interval is larger than 87.5% and less than 150% of the RRavg. The first qualified beat is available only after an initial RRavg value is calculated.

Heart rate is classified as "regular" if at least 40% of the beats are regular. According to one approach, heart rate regularity is checked. If the rate is not regular, the SVR characterization is suspended until the next scheduled SVR characterization time. By this method, the RRavg and rate regularity are continuously calculated for every beat during the SVR characterization procedure. If the rate becomes too high, or the rate becomes irregular at any stage of the SVR characterization procedure, the SVR characterization is suspended immediately.

Initiating SVR characterization in accordance with an embodiment of the present invention includes performing shock channel automatic gain control (AGC) adjustment 620. Shock channel AGC is performed in this embodiment by measuring the peak value in four regular beats and adjusting the shock channel gain such that the averaged peak value is 50% of the maximum A/D converter value. After the SVR characterization procedure is completed, shock channel AGC is readjusted until the next update.

Figure 7:
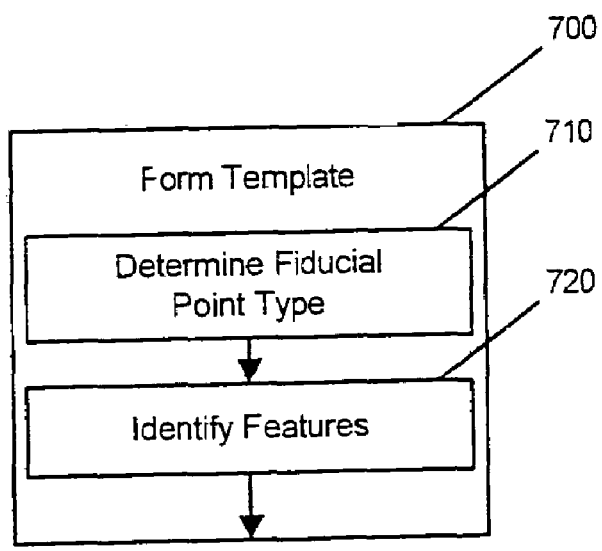
FIG. 7 is a flowchart of a method of forming a template in accordance with an embodiment of the present invention.

FIG. 7 provides a more detailed illustration of the processes associated with forming a template in accordance with an embodiment of the present invention. In general terms, a template is a combination of one or more beats, wherein the combination of beats may represent one beat of the patient's supraventricular rhythm. According to this embodiment, a template is formed by determining the fiducial point type and the fiducial point of the rate channel signal of the initial template beat, and identifying the value and location of features of the initial shock channel waveform relative to the rate channel fiducial point.

Figure 12:
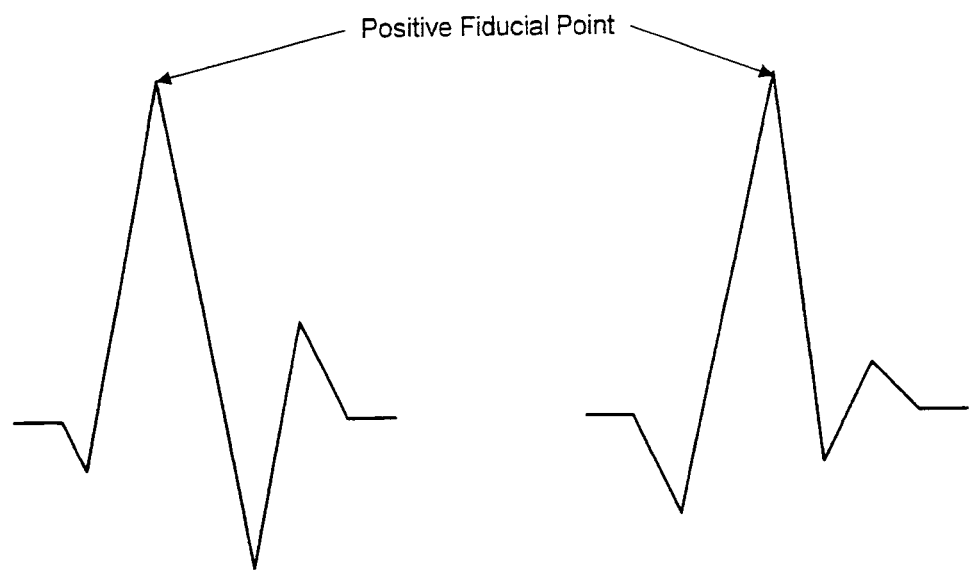
FIGS. 12 and 13 respectively illustrate positive and negative type fiducial points determined from rate channel signals in accordance with an embodiment of the present invention.
Figure 13:
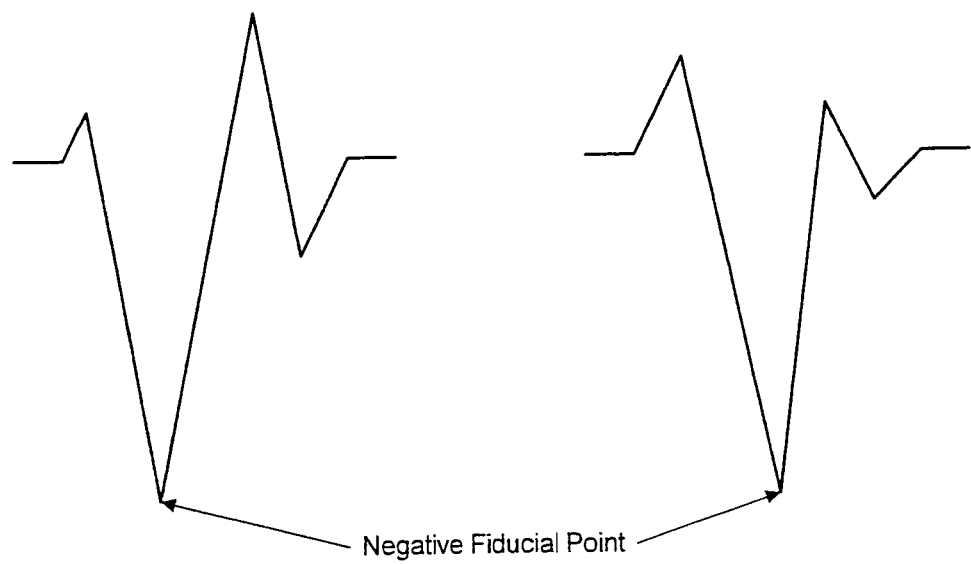

A fiducial point represents a peak value of the rate channel signal. A fiducial point type is either positive (Pos), associated with a positive peak, or negative (Neg), associated with a negative peak. When a template is formed, the positive peak (Pos) or the negative peak (Neg) of the rate channel signal used to form the template determines the fiducial point type of the template. FIGS. 12 and 13 depict positive and negative fiducial points, respectively. The Pos and Neg peaks are measured as absolute values. The fiducial point type is determined by Equation 2 as follows:

If Pos>0.9*Neg, the fiducial point type is positive

If Pos≦0.9*Neg, the fiducial point type is negative  [2]

If a stored template exists, the fiducial point type of the stored template is used as the fiducial point type of the template. If no stored template exists, the fiducial point type of the first beat used to form the template is used as the fiducial point type for the template.

Returning to FIG. 7, when a template is formed 700, a fiducial point type is determined 710 as set forth in the above paragraph, and one or more features of the shock channel waveform are identified 720. In one embodiment of the invention, and with reference to FIGS. 14 and 15, five features are initially identified for the shock channel template, followed by three additional features determined at midpoints between certain ones of the five initially selected features.

Feature 3 is selected as the absolute maximum peak in a feature window defined by 31 samples centered at the fiducial point. If the positive peak amplitude is equal to the negative peak amplitude, the positive peak is selected as Feature 3.

Feature 2 is found by searching backward from Feature 3 until a point is reached that meets the following conditions: 1) the search is limited to 10 samples. If no point satisfies the following conditions, then the 10th sample becomes Feature 2; 2) the amplitude is less than 25% of the maximum peak; 3) a turning point is found or the slope is flat, and 4) Feature 2 is at least 4 samples away from Feature 3.

By way of example, let Q(I) represent the current sample. A turning point is found if:

$Q(I-1) \geq Q(I)$ and $Q(I) < Q(I+1)$ for a positive Feature 3

$Q(I-1) \leq Q(I)$ and $Q(I) > Q(I+1)$ for a negative Feature 3  [3]

Figure 14:
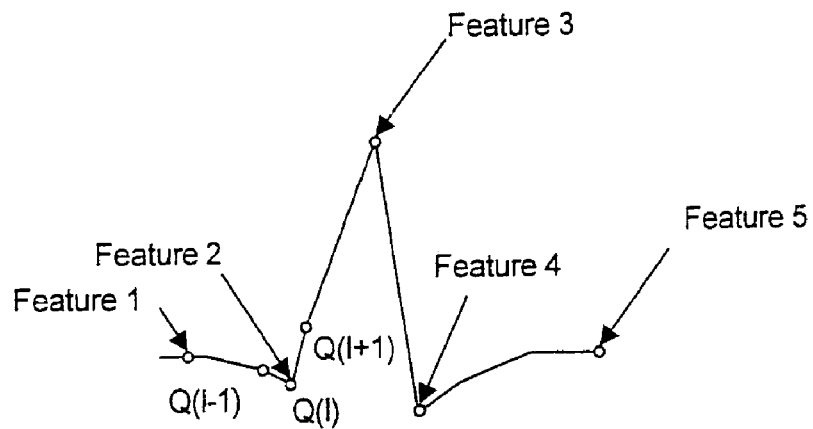
FIGS. 14 and 15 show morphological features, including turning point and flat slope features, respectively, for selection of Feature 2 in accordance with an embodiment of the present invention.

As is shown in FIG. 14, Q(I) is selected as Feature 2. As such, Feature 2 is selected as a turning point.

Figure 15:
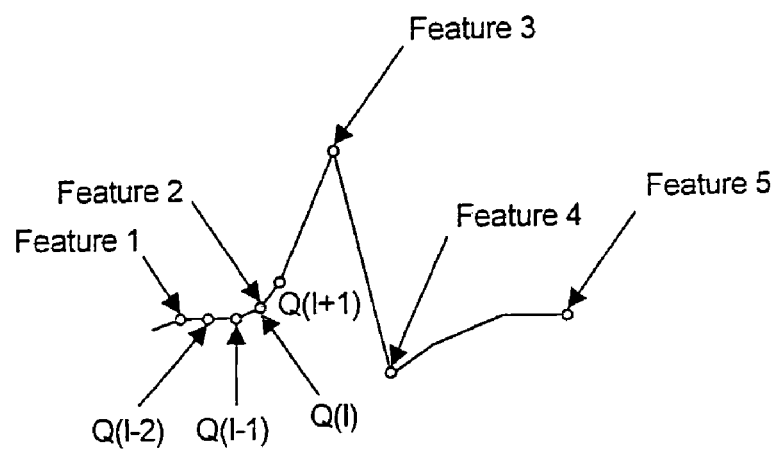

The slope is considered flat, as shown in FIG. 15, if abs(Q(I+1)−Q(I−1))<4 and abs(Q(I+1)−Q(I−2))<4, in the case when the A/D converter maximum value is 128. In the illustrative depiction of FIG. 15, Q(I) is selected as Feature 2. As such, Feature 2 is selected as a flat slope point.

Feature 4 is found by searching forward starting from Feature 3 until a point is reached that meets the following conditions: 1) the search is limited to 16 samples. If no point satisfies the following conditions, then the 16th sample becomes Feature 4; 2) the amplitude is less than 25% of the maximum peak; and 3) a turning point is found or the slope is flat.

By way of example, let Q(I) represent the current sample. A turning point is found if $Q(I+1) \geq Q(I)$ and $Q(I) < Q(I-1)$ for a positive Feature 3

$Q(I+1) > Q(I)$ and $Q(I) > Q(I-1)$ for a negative Feature 3  [4]

Figure 16:
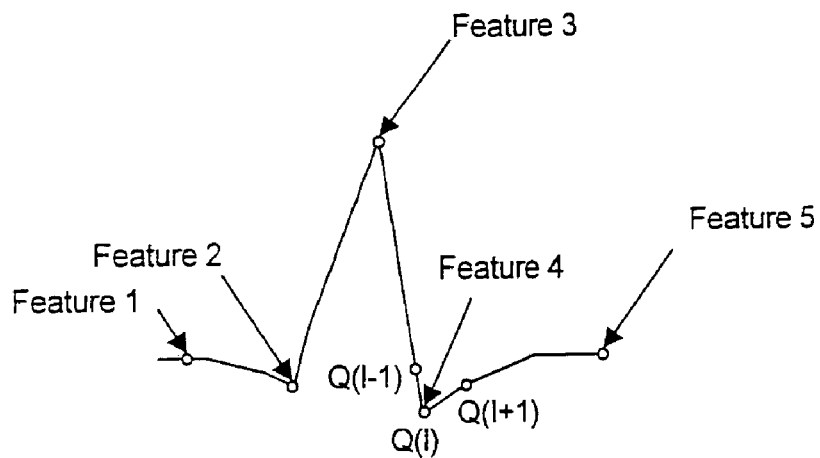
FIGS. 16 and 17 show morphological features, including turning point and flat slope features, respectively, for selection of Feature 4, in accordance with an embodiment of the present invention.

Q(I) is selected as Feature 4, as is shown in FIG. 16.

Figure 17:
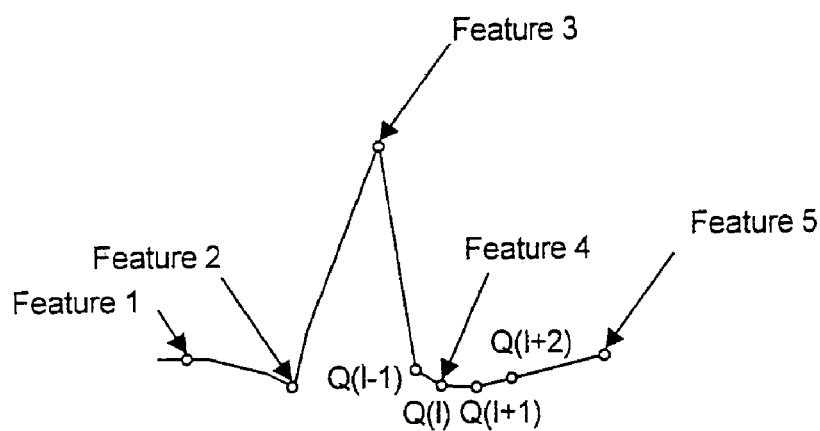

The slope is flat, as shown in FIG. 17, if abs(Q(I−1)−Q(I+1))<4 and abs(Q(I−1)−Q(I+2))<4. In this case, Q(I) is selected as Feature 4.

Feature 1 is selected as the seventeenth sample from the beginning of the detection window. Feature 5 is selected as the last sample of the detection window. Three additional features are selected at the midpoint of Features 1 and 2, the midpoint of Features 2 and 3, and the midpoint of Features 3 and 4, respectively. If a midpoint falls between two sample points, the leftmost (earlier in time) point is selected. Thus, according to this embodiment, eight feature values (e.g., amplitudes) and their associated locations with respect to the fiducial point and the corresponding fiducial point type are saved for SVR characterization.

Figure 8:
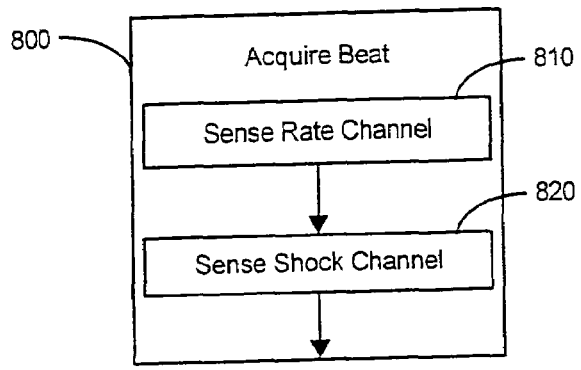
FIG. 8 is a flowchart of a method of acquiring a beat in accordance with an embodiment of the present invention.

FIG. 8 provides a more detailed illustration of the process of acquiring a beat in accordance with an embodiment of the present invention. As discussed above, cardiac signals sensed through use of the RV-tip electrode are rate channel signals. Cardiac signals sensed through use of one or both of the defibrillation coils or electrodes are shock channel signals. When a beat is acquired, the rate channel signal is sensed 810 and the shock channel signal is sensed 820.

Figure 9:
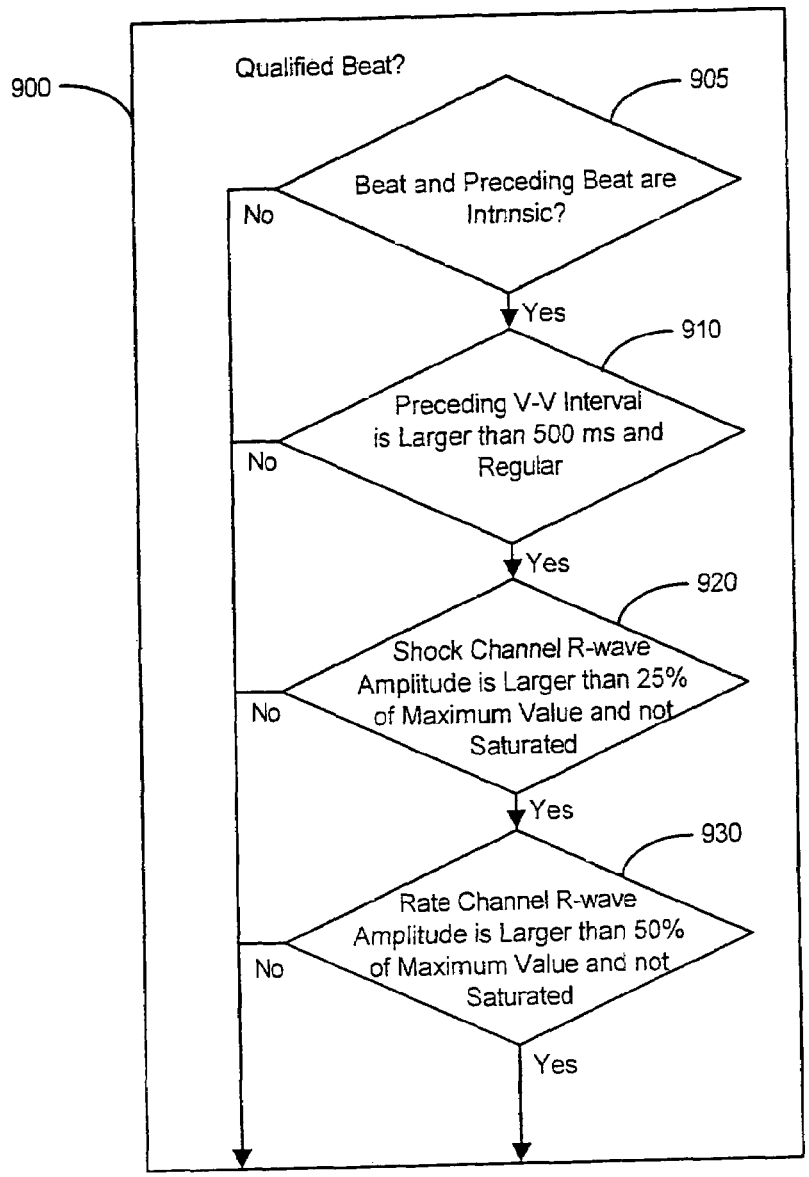
FIG. 9 is a flowchart of a method of determining if a beat is a qualified beat in accordance with an embodiment of the present invention.

FIG. 9 illustrates a method of determining if a beat is a qualified beat in accordance with the present invention. Four criteria must be present for a beat to be considered a qualified beat suitable for forming or updating a template. First, the beat and the preceding beat must be intrinsic beats 905. Second, the preceding beat must have a V-V interval larger than approximately 500 ms and the beat must be regular 910. Third, the shock channel R-wave amplitude must be larger than approximately 25% of the maximum value of the A/D converter and must not be saturated 920. Finally, the rate channel R-wave amplitude must be larger than approximately 50% of the maximum value of the A/D converter and must not saturate the A/D converter at more than one consecutive sample point 930. If all four of these conditions are detected, then the beat is a qualified beat suitable for characterizing the patient's supraventricular rhythm.

Figure 10:
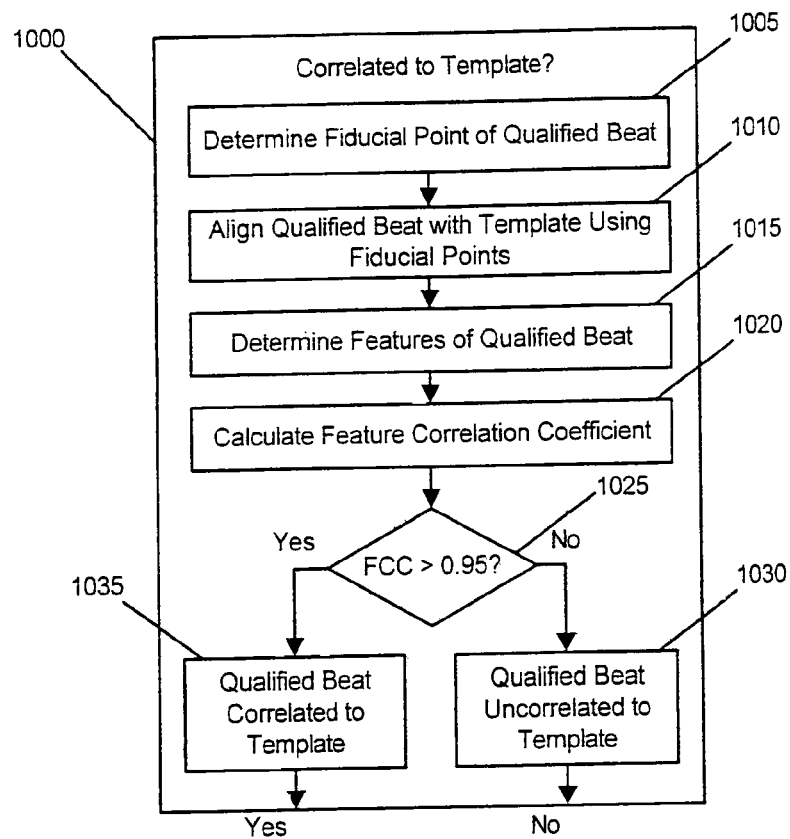
FIG. 10 is a flowchart of a method of determining if a beat is correlated to a template in accordance with an embodiment of the present invention.

Turning now to FIG. 10, a more detailed illustration of various steps associated with determining if a qualified beat is correlated to a template in accordance with an embodiment of the present invention is provided. The method illustrated in FIG. 10 may be used to determine if a beat is correlated to the first or the second template. According to this method, the fiducial point is determined from the rate channel signal of the qualified beat 1005. The shock channel waveforms of the template and the qualified beat are aligned using the fiducial points of the template and the qualified beat 1010. A number of features of the qualified beat are determined at the locations relative to the fiducial point previously determined for the template 1015. The template and the qualified beat are compared by calculating a feature correlation coefficient (FCC) 1020. In one particular embodiment, Equation 5, provided below, is used to compute the FCC between the template features and the beat features.

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [5]$$

where, Xi represents template N features and Yi represents beat N features, and N=8 in this illustrative example. The sign of the numerator term is checked before squaring. If the numerator is negative, the beat is uncorrelated, and the remainder of the computation need not be performed.

If the FCC is greater than a predetermined value, as tested at block 1025, for example 0.95, then the qualified beat is correlated 1035 to the template. If the FCC is less than or equal to the predetermined value, then the qualified beat is uncorrelated 1030 to the template.

Figure 11:
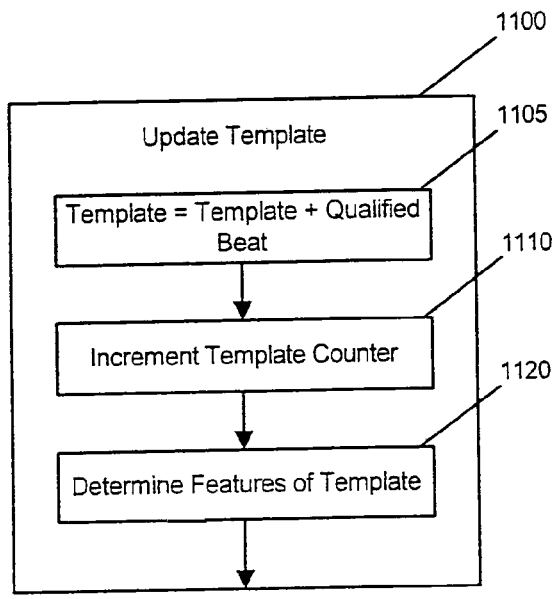
FIG. 11 is a flowchart of a method of updating a template in accordance with an embodiment of the present invention.

FIG. 11 illustrates a method of updating a template with a qualified beat correlated to the template in accordance with an embodiment of the invention. The template may be updated by point-by-point addition 1105 of the qualified beat to the template, the updated template being the sum of the addition. The template counter is incremented 1110. The features of the updated template are identified 1120.

When a qualified beat is correlated to a template, it represents a template beat and is used to update the template. After temporal alignment using the rate channel fiducial points, the shock channel waveforms of the template and the qualified beat may be combined by point by point addition. For example, the template may be characterized by the following equation:

$$\text{Template}(i, j) = \sum_{i=1}^{N} \text{Template Beat}(i, j) \quad [6]$$

where the term Template Beat(i,j) is the $j^{th}$ sample of the $i^{th}$ template beat of the template, and the initial template is designated as the template beat for i=1.

Figure 18:
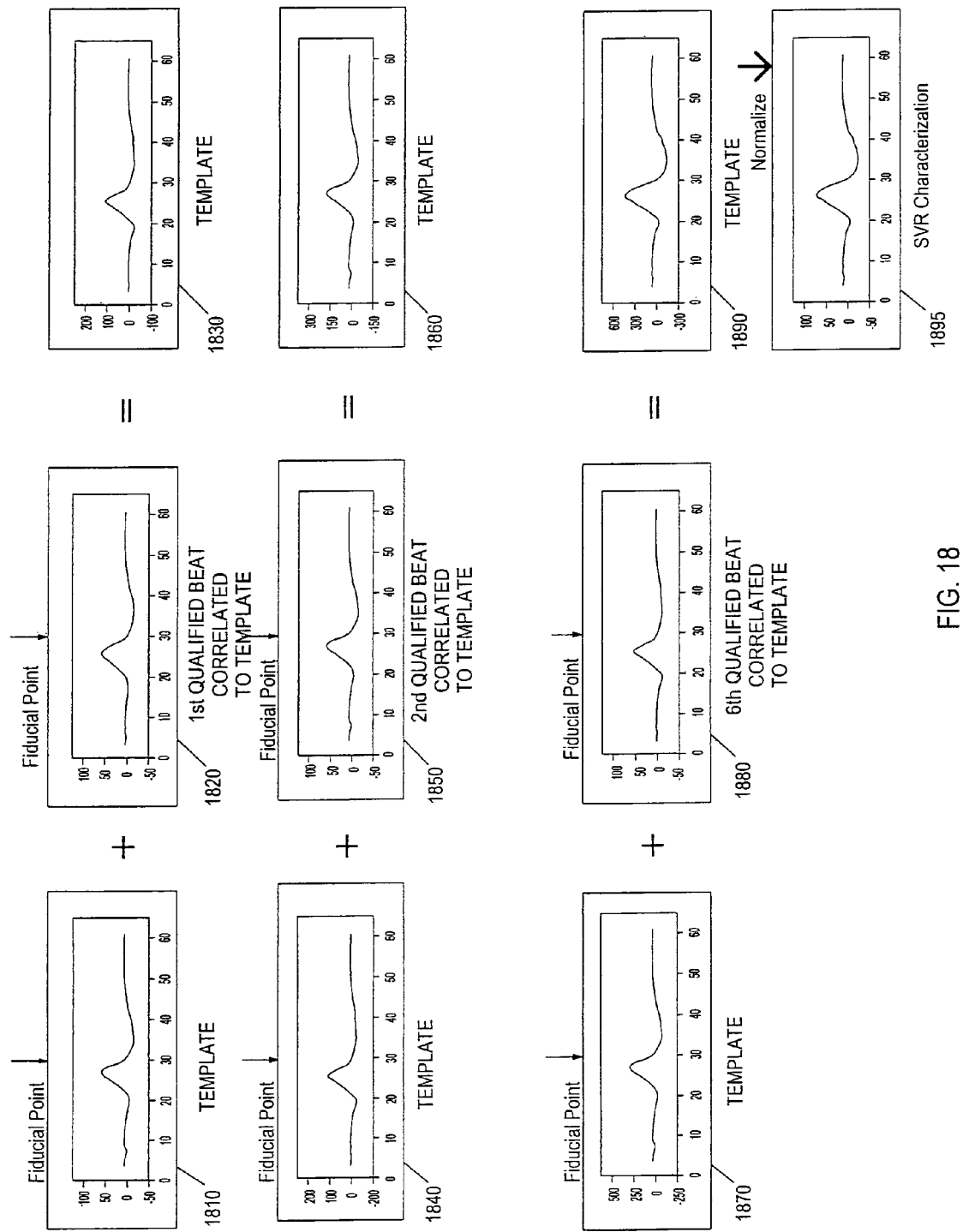
FIG. 18 illustrates a method of updating a template by point-by-point addition of a number of template beats aligned with respect to a rate channel fiducial point in accordance with an embodiment of the present invention.

The procedure of template updating is illustrated diagrammatically in FIG. 18. The shock channel waveform of the initial template representing the first template beat 1810 is temporally aligned to the shock channel waveform of the first qualified beat correlated to the template 1820 using the rate channel fiducial points. The template beats are combined by point by point addition of j samples of the two beats 1830. The sum of the addition becomes the updated template 1840. The updated template 1840 is added in the same manner to the next qualified beat 1850 which is correlated to the updated template. This process continues until all the qualified beats have been combined 1890. In an example of this method discussed previously, the number of qualified beats combined is six. The updated template 1890 may be normalized by dividing by samples of the updated template by one plus the number of qualified, correlated beats used to form the updated template, in this example, six. The normalized, updated template is stored as a characterization of the patient's supraventricular rhythm 1895.

Characterization of a patient's supraventricular rhythm in accordance with the principles of the present invention provides for several advantages. For example, the method of template generation of the present invention requires only beat-by-beat analysis and is efficient in memory usage making it well-suited for use in implantable devices, such as in implantable cardioverter/defibrillator devices. Further, template generation is possible using a relatively small number of beats as compared to previous methods, making the template generation method of the present invention particularly useful when the patient's heart is being intermittently or constantly paced.

Systems and methods of the present invention have been described in the above discussion using illustrative examples wherein two templates are used to characterize a patient's supraventricular rhythm. The systems and methods of the invention, however, are not limited to use of two templates and may be extended to any number of templates. In some cases, particularly where the morphology of successive cardiac beats varies significantly, it may be beneficial to provide three or more templates for SVR characterization. Extending the example described above to N templates, a detected qualified beat may be compared to each of N templates to determine correlation. When a qualified beat is correlated to a specific template, such as template x for example, template x is updated with the qualified beat and the template x counter is updated. When one of the N template counters is equal to a predetermined number of beats, the template corresponding to that template counter is stored as a characterization of the patient's supraventricular rhythm. In this way, any number of additional templates and additional template counters may be readily incorporated into the algorithm as desired.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of characterizing a patient's cardiac rhythm in an implantable device, comprising:
    detecting a cardiac beat;
    extracting feature timing information from the cardiac beat and each template of a plurality of templates;
    temporally aligning the cardiac beat with at least one template of the plurality of templates based on the feature timing information;
    selectively updating the plurality of templates using the aligned cardiac beat;
    associating a plurality of counters with the plurality of templates, and each time a template is updated incrementing a counter associated with the updated template; and
    identifying a particular template of the plurality of templates as representative of the cardiac rhythm.

2. The method of claim 1, wherein detecting the cardiac beat comprises detecting a two channel cardiac beat signal.

3. The method of claim 1, wherein aligning the cardiac beat signal and the at least one template comprises:
    extracting a fiducial point of the cardiac beat;
    extracting a fidicial point of the at least one template; and
    temporally aligning the cardiac beat and the template based on the extracted fiducial points.

4. The method of claim 3, wherein selectively updating the plurality of templates comprises:
    extracting features from the aligned cardiac beat having predetermined temporal relationships to the fiducial point of the at least one template; and
    updating the at least one template using the cardiac beat if the extracted features are similar to corresponding template features.

5. The method of claim 1, wherein selectively updating the plurality of templates using the aligned cardiac beat comprises:
    calculating a feature correlation coefficient for the cardiac beat and a template of the plurality of templates; and
    updating the template if the feature correlation coefficient is greater than a predetermined value.

6. The method of claim 1, wherein identifying the particular template comprises identifying the particular template as representative of the cardiac rhythm based on a number of times the particular template is updated.

7. The method of claim 1, wherein identifying the particular template comprises:
identifying the particular template as representative of the cardiac rhythm if the particular template has a highest counter value of the plurality of counters.

8. The method of claim 1, wherein identifying the particular template comprises:
identifying the particular template a representative of the cardiac rhythm if the counter for the particular template reaches a predetermined value before the counters for other templates reach the predetermined value.

9. The method of claim 1, further comprising:
retrieving at least one template of the plurality of templates from memory; and
generating at least one template of the plurality of templates using a previous cardiac beat.

10. A body implantable system for characterizing cardiac rhythms, comprising:
a sensing system comprising electrodes electrically coupled to a heart, the sensing system configured to detect a cardiac beat;
a control system coupled to the sensing system, the control system configured to temporally align the cardiac beat with at least one template of a plurality of templates based on feature timing information extracted from the cardiac beat and the templates, selectively update the plurality of templates using the aligned cardiac beat, and identify a particular template of the plurality of templates as representative of the cardiac rhythm; and
counters associated with the plurality of templates, wherein the counters are selectively incremented each time a template is updated.

11. The system of claim 10, further comprising a memory, wherein the control system retrieves at least one template of the plurality of templates from the memory.

12. The system of claim 10, wherein the control system is configured to generate a new template using the cardiac beat if no templates are similar to the cardiac beat.

13. The system of claim 10, wherein:
the feature timing information extracted from the cardiac beat comprises a fiducial point of the cardiac beat; and
the feature timing information extracted from the templates comprises fidicial points of the templates.

14. The system of claim 10, wherein:
the feature timing information extracted from the cardiac beat comprises a peak value of the cardiac beat; and
the feature timing information extracted from the templates comprises peak values of the templates.

15. The system of claim 1, wherein the control system is configured to identify the particular template as representative of the cardiac rhythm based on a value of a counter associated with the particular template.

16. The system of claim 1, wherein the control system is configured to identify the particular template as representative of the cardiac rhythm if the particular template has a counter value higher than that of the counters associated with other templates.

17. The system of claim 1, wherein the control system is configured to identify the particular template as representative of the cardiac rhythm if a counter associated with the particular template reaches a predetermined value before counters associated with other templates.

18. An implantable cardiac system, comprising:
means for aligning a cardiac beat with each template of a plurality of templates based on feature timing information extracted from the cardiac beat and the templates;
means for selectively updating one or more templates of the plurality of templates using the aligned cardiac beat;
means for associating a plurality of counters with the plurality of templates, and for selectively incrementing the counters each time a template is updated; and
means for identifying a particular template of the selectively updated templates as representative of the cardiac rhythm.

19. The system of claim 18, further comprising:
means for retrieving at least one template of the plurality of templates from memory; and
means for generating at least one template of the plurality of templates using a previous cardiac beat.

20. The system of claim 18, wherein the identifying means identifies the particular template as representative of the cardiac rhythm based on a value of the counter associated with the particular template.

* * * * *